(12) United States Patent
Johansen et al.

(10) Patent No.: US 12,285,925 B2
(45) Date of Patent: *Apr. 29, 2025

(54) FILMS AND LAMINATES FOR USE IN PACKAGING REACTIVE COMPOUNDS

(71) Applicant: adapa flexibles Denmark Slagelse A/S, Slagelse (DK)

(72) Inventors: Peter Johansen, Odense C (DK); Lars Christensen, Slagelse (DK); Torben Fogtmann, Nyborg (DK)

(73) Assignee: adapa flexibles Denmark Slagelse A/S, Slagelse (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,746

(22) Filed: May 3, 2022

(65) Prior Publication Data

US 2022/0258454 A1 Aug. 18, 2022

Related U.S. Application Data

(62) Division of application No. 16/425,067, filed on May 29, 2019, now Pat. No. 11,325,350.

(30) Foreign Application Priority Data

Aug. 8, 2018 (EP) .................................... 18187923

(51) Int. Cl.
*B32B 15/085* (2006.01)
*A61K 9/00* (2006.01)
(Continued)

(52) U.S. Cl.
CPC .......... *B32B 15/085* (2013.01); *A61K 9/0014* (2013.01); *A61K 9/7084* (2013.01);
(Continued)

(58) Field of Classification Search
CPC .. A61K 31/167; A61K 31/27; A61K 31/4468; A61K 31/465; A61K 9/0014;
(Continued)

(56) References Cited

U.S. PATENT DOCUMENTS 5,613,958 A 3/1997 Kochinke et al.
6,120,860 A 9/2000 Bowen et al.
(Continued)

FOREIGN PATENT DOCUMENTS

BR 102015012729 A2 1/2017
CN 103269698 A 8/2013
(Continued)

OTHER PUBLICATIONS

Database WPI Week 201579, Derwent Publications Ltd., London, GB; AN 2015-71769A, XP002759263; 2 pgs.
(Continued)

*Primary Examiner* — Frances Tischler
(74) *Attorney, Agent, or Firm* — Holland & Hart LLP (57) ABSTRACT

The present disclosure relates to a laminate film including a water resistant or oxygen resistant base layer, and co-extrusion layer. The co-extrusion layer may include a tie layer and a contact layer, and the contact layer may include a polymer such as cyclic olefin copolymer, a polyamide, or an ethylene vinyl alcohol. A total loading of the tie layer may be in the range of 3-9 g/m$^2$ and wherein a loading of the contact layer is: loading$_{contact}$=x*loading$_{tie}$, wherein loading$_{contact}$ is the loading of the contact layer, loading$_{tie}$ is the total loading of the tie layer, and x is in the range of 0.8 to 3.

14 Claims, 2 Drawing Sheets

(51) Int. Cl.

| | | |
|---|---|---|
| *A61K 9/70* | (2006.01) | |
| *A61K 31/167* | (2006.01) | |
| *A61K 31/27* | (2006.01) | |
| *A61K 31/4468* | (2006.01) | |
| *A61K 31/465* | (2006.01) | |
| *B32B 27/30* | (2006.01) | |
| *B32B 27/32* | (2006.01) | |
| *B32B 37/02* | (2006.01) | |
| *B65D 65/40* | (2006.01) | |

(52) U.S. Cl.
CPC ............ *A61K 31/167* (2013.01); *A61K 31/27* (2013.01); *A61K 31/4468* (2013.01); *A61K 31/465* (2013.01); *B32B 27/30* (2013.01); *B32B 27/325* (2013.01); *B32B 37/02* (2013.01); *B65D 65/40* (2013.01); *B32B 2307/7244* (2013.01); *B32B 2307/7265* (2013.01); *B32B 2439/46* (2013.01)

(58) Field of Classification Search
CPC .... A61K 9/7084; B32B 15/08; B32B 15/082; B32B 15/085; B32B 15/20; B32B 2255/10; B32B 2255/20; B32B 2307/718; B32B 2307/7244; B32B 2307/7246; B32B 2307/7265; B32B 2439/46; B32B 2439/80; B32B 2556/00; B32B 27/08; B32B 27/283; B32B 27/30; B32B 27/304; B32B 27/306; B32B 27/325; B32B 27/34; B32B 27/36; B32B 37/02; B65D 65/40
See application file for complete search history.

(56) References Cited

U.S. PATENT DOCUMENTS

| | | |
|---|---|---|
| 6,670,423 B2 | 12/2003 | Hausmann |
| 6,891,018 B2 | 5/2005 | Murakami et al. |
| 6,903,161 B2 | 6/2005 | Morris |
| 6,921,563 B2 | 7/2005 | Goerlitz et al. |
| 8,003,179 B2 | 8/2011 | Merical et al. |
| 8,703,283 B2 | 4/2014 | Goerlitz et al. |
| 8,722,164 B2 | 5/2014 | Bekele et al. |
| 9,487,918 B2 | 8/2016 | Geerdinck et al. |
| 9,452,593 B2 | 9/2016 | Tatarka et al. |
| 9,663,281 B2 | 5/2017 | Hall et al. |
| 10,889,093 B2 | 1/2021 | Wang |
| 2004/0234790 A1 | 11/2004 | Smith et al. |
| 2005/0037162 A1 | 2/2005 | Adams |
| 2005/0112337 A1 | 5/2005 | Jester |
| 2006/0198973 A1 | 9/2006 | Jester |
| 2008/0286512 A1 | 11/2008 | Holzmuller et al. |
| 2009/0208685 A1 | 8/2009 | Rivers et al. |
| 2011/0158564 A1 | 6/2011 | Krumme |
| 2014/0323996 A1 | 10/2014 | Langer et al. |
| 2015/0225151 A1 | 8/2015 | Osborn et al. |
| 2016/0325534 A1 | 11/2016 | Hu et al. |
| 2017/0158400 A1 | 6/2017 | Priscal et al. |
| 2017/0348246 A1 | 12/2017 | Tohara et al. |
| 2018/0354702 A1 | 12/2018 | Liu et al. |

FOREIGN PATENT DOCUMENTS

| | | |
|---|---|---|
| DE | 202008017320 U1 | 5/2009 |
| DE | 102012113026 A1 | 6/2014 |
| DE | 102013113718 A1 | 6/2015 |
| EP | 1364777 B1 | 8/2005 |
| EP | 1769908 A1 | 4/2007 |
| EP | 1525092 B1 | 5/2007 |
| EP | 1775122 B1 | 9/2014 |
| EP | 2939667 A1 | 11/2015 |
| EP | 3000750 A1 | 3/2016 |
| EP | 1475228 B1 | 7/2017 |
| EP | 2907769 B1 | 9/2017 |
| EP | 2349867 B1 | 10/2017 |
| EP | 3144127 B1 | 1/2018 |
| EP | 3112384 B1 | 7/2018 |
| EP | 3360530 A1 | 8/2018 |
| EP | 2986450 B1 | 1/2019 |
| EP | 3210907 B1 | 7/2019 |
| WO | WO-1991009731 A1 | 7/1991 |
| WO | WO-1995007816 A1 | 3/1995 |
| WO | WO-2000044559 A1 | 8/2000 |
| WO | WO-2001064786 A1 | 9/2001 |
| WO | WO-2005037539 A1 | 4/2005 |
| WO | WO-2005097486 A1 | 10/2005 |
| WO | WO 2009/105205 A1 | 8/2009 |
| WO | WO-2010047906 A1 | 4/2010 |
| WO | WO-2010075946 A1 | 7/2010 |
| WO | WO 2012/037180 A1 | 3/2012 |
| WO | WO-20121192271 A1 | 9/2012 |
| WO | WO-2013004243 A1 | 1/2013 |
| WO | WO-2013028398 A1 | 2/2013 |
| WO | WO-2013034273 A1 | 3/2013 |
| WO | WO-2013116445 A1 | 8/2013 |
| WO | WO-2014023995 A1 | 2/2014 |
| WO | WO-2015097208 A1 | 7/2015 |
| WO | WO-2015118215 A1 | 8/2015 |
| WO | WO-2015123211 A1 | 8/2015 |
| WO | WO-2015174502 A1 | 11/2015 |
| WO | WO-2015187173 A1 | 12/2015 |
| WO | WO-2015187174 A1 | 12/2015 |
| WO | WO-2015199637 A1 | 12/2015 |
| WO | WO-2016076844 A1 | 5/2016 |
| WO | WO-2016164794 A1 | 10/2016 |
| WO | WO-2016190081 A1 | 12/2016 |
| WO | WO-2016194555 A1 | 12/2016 |
| WO | WO-2016200363 A1 | 12/2016 |
| WO | WO-2017034560 A1 | 3/2017 |
| WO | WO-2017063087 A1 | 4/2017 |
| WO | WO-2017087032 A1 | 5/2017 |
| WO | WO-2017100182 A1 | 6/2017 |
| WO | WO-2017100358 A1 | 6/2017 |
| WO | WO-2017114922 A1 | 7/2017 |
| WO | WO-2017189836 A1 | 11/2017 |
| WO | WO-2017217989 A1 | 12/2017 |
| WO | WO-2018028996 A1 | 2/2018 |
| WO | WO-2018041320 A2 | 3/2018 |
| WO | WO-2018222864 A1 | 12/2018 |
| WO | WO-2018231219 A1 | 12/2018 |

OTHER PUBLICATIONS

Morris, "The Science and Technology of Flexible Packaging, Multilayer Films from Resin and Process to End Use", published by Elsevier, Inc., 2017, 709 pages.

Wypych, "Handbook of Polymers", ChemTech Publishing, Toronto, Ontario Canada, 2012, 31 pages.

Judgement and Order—PGR2023-0008, U.S. Pat. No. 11,260,624 B2 in the United States Patent & Trademark Office, Before the Patent Trial and Appeal Board, *Huhtamaki Flexible Packaging Germany Gmbh & Co. KG*, Petitioner v. *Adapa Flexibles Slagelse A/S f/k/a/ Danapak Flexibles A/S*, Patent Owner, dated Jun. 18, 2024, 78 pages.

FILMS AND LAMINATES FOR USE IN PACKAGING REACTIVE COMPOUNDS

CROSS-REFERENCE TO RELATED APPLICATIONS

The present Application for Patent claims priority to U.S. patent application Ser. No. 16/425,067 by Johansen et al., entitled "IMPROVED FILMS AND LAMINATES FOR USE IN PACKAGING REACTIVE COMPOUNDS," filed May 29, 2019, which claims the benefit of European Patent Application No. 18187923.0, entitled "IMPROVED FILMS AND LAMINATES FOR USE IN PACKAGING REACTIVE COMPOUNDS," filed Aug. 8, 2018, each of which is assigned to the assignee hereof, and each of which is expressly incorporated by reference in its entirety herein.

TECHNICAL FIELD

The present disclosure relates to improved laminates whereby a tie layer and a contact layer are coextruded with a base layer, such as a metal foil, as well as uses of the films and laminates to wrap APIs such as nicotine, fentanyl, lidocaine and rivastigmine and in which a specific ratio of tie to contact layer provides good mechanical properties and improved sealing properties.

BACKGROUND

In the pharmaceutical industry substances, including highly aggressive substances such as nicotine, fentanyl, rivastigmine and lidocaine are packed as tablets in inhalers, patches etc. resulting in special requirements for the packaging, laminate, or film for sealing these substances in order to ensure that no adverse degradation or uptake takes place.

One common example is the problem relating to the packaging of nicotine, in particular as nicotine patches, because nicotine is highly aggressive towards its environment and highly volatile. These properties are problematic for the consumer safety and product durability if not addressed, because it is important that the amount of nicotine in, for example a tablet, gum or a patch is stable and complies with the product specification. Further, it is important to avoid adverse reactions between the packaging and the pharmaceutical substance. Additionally, from a business perspective a long stable shelf time is highly desirable. Thus, the chemical requirements of a packaging, film or laminate are typically:

Mechanically stable laminate that does not separate or deform
Ensuring that the packaging is child proof to increase safety of potentially hazardous compounds
Inert properties ensuring that chemical compounds do not migrate from the exterior environment of a laminate through the laminate and getting into contact with a sealed substance; and
That the enclosed API does not react with the surface with which it is in contact or migrate through it.

A known polymer that fulfils the requirements of extreme chemical resistance and inert properties is a polyactylloni-trile (PAN) based film, which is sold for example as resins under the trademark Barex®, which is manufactured i.a. by the company Ineos. Barex® is widely used and approved for drugs and food applications and is used because it is a good barrier towards oxygen, nitrogen and carbon dioxide compared to other common polymers, and because it has excellent chemical resistance towards different functional groups such as hydrocarbons, ketones, esters, alcohols, bases and acids and/or pharmaceuticals such as nicotine.

Furthermore, extruded Barex® resin is heat stable and therefore weldable at a temperature around 160-220° C., which makes it suitable for use in flexible packaging. However, Barex® is sold at a high price due to the difficulties in its production and subsequent extrusion to a film which results in a high loss of material. Furthermore, the water and oxygen resistance of Barex® is not satisfactory for all purposes.

Another solution can be found in WO 00/44559 disclosing a material for packaging nicotine containing products (e.g. patches, tablets, lozenges, nasal spray), wherein the material comprises a polymer based on dimethyl-2,6-naphthalene dicarboxynate and/or 2,6-naphthalene dicarboxylic acid monomers. Further, it is disclosed that a polymeric film is combined with other barrier materials in a laminate to further improve the barrier characteristic of the laminate. The preferred material for a laminate is aluminium due to its good oxygen and water barrier properties.

A further solution is found in WO 2017/114922 of the present applicant, which discloses a film having a co-extrusion layer comprising a tie layer and a contact layer, said contact layer is the innermost layer facing an aggressive chemical pharmaceutical such as rivastigmine, nicotine, fentanyl or lidocaine. The contact layer may comprise polyamide, cyclic olefin copolymer, or an ethylene vinyl alcohol. The tie layer is co-extrusion coated to a base layer so that the tie layer is in contact with the base layer and the contact layer.

A further solution is described in WO 2015/123211 disclosing a film having a tie layer and a contact layer comprising COC facing a pharmaceutical such as nicotine. The film may be produced by providing a co-extrusion layer comprising a tie layer and a contact layer, which is coated onto aluminum foil.

Hence, given the increased market and demands for packaging, there is an instant need for finding various solutions for producing strong laminates in a cost efficient manner.

SUMMARY

With this background it is an object of the present disclosure to provide solutions that meet one or more of the needs described above, that is, i.a. solutions that provide impermeability and inertness to a packaging, while still providing a mechanically strong laminate that does not separate or deform, puncture, is sealable and otherwise resistant to mechanical impact.

Accordingly, in a first aspect this is solved by providing a laminate film comprising at least a base layer, which is water and/or oxygen resistant, and a co-extrusion layer, said co-extrusion layer comprising a tie layer and a contact layer, wherein the contact layer comprises a polymer selected from the group consisting of a cyclic olefin copolymer, a polyamide, or, an ethylene vinyl alcohol, and wherein the total loading of the tie layer is in the range of 3-12 g/m² and wherein the loading of the contact layer is:

$loading_{contact} = x \cdot loading_{tie}$, where x is in the range of 0.8 to 3, preferably 1 to 3, more preferred 1.33 to 2.75.

It has been found that when the tie layer and the contact layer are coextruded according to the present disclosure, the loading of the tie layer is of unexpected importance to a good processability of the final film, laminates and wrappings made of the film.

The loading according to the present disclosure of the co-extrusion layers also unexpectedly resulted in a better adherence of the various layers after co-extrusion resulting in a homogenous film where the individual layers do not separate.

It has further been found that in addition to a better production, the chemical resistance of the film is also improved by reducing the loading of the tie layer relative to the contact layer.

While it was previously believed that the tie layer did not contribute significantly to the chemical resistance of the film but only the stability of the laminate, the present inventors have unexpectedly found that by providing a tie layer with a relatively low loading and a contact layer which has approximately the same or higher loading than the tie layer, preferably a higher loading, an improved inertness and/or uptake API, such as nicotine, rivastigmine, fentanyl, and lidocaine, was obtained. While at the same time laminates were provided with better or at least as good mechanical properties as prior art products.

Hence, contrary to what was previously believed a smaller tie layer combined with same or larger contact layer provides better overall properties to the final laminate or film.

In a preferred embodiment the tie layer is multilayered. When the tie layer is a multilayer a first tie layer is the layer adjacent to the contact layer. The numbering of the layers of the multilayered tie layer hence ascends the closer a layer is to the base layer. For example, if the multilayered tie layer consists of two layers, the film has the following structure of:

Base layer/second tie layer/first tie layer/contact layer (the latter three being coextruded).

A polymer candidate for use as a tie layer or contact layer in the context of the present disclosure may be selected by calculating the RED value, which is generally used to predict the solubility of a polymer in a particular solvent, or the compatibility of two polymers in a blend. Accordingly, the RED values for various polymer/solvent systems have been calculated, wherein the polymer is the polymer forming the contact layer, or, a polymer for use as a tie layer, and the solvent is an aggressive chemical substance such as nicotine, rivastigmine, fentanyl and lidocaine etc.

The RED value for the polymer and the aggressive chemical substance is calculated by using the theory of the Hansen solubility Parameters (HSP), which is described in C. M. Hansen: "Hansen Solubility Parameters, A User's Handbook", CRC Press, Boca Raton, 1999.

The HSP system between the polymer and the aggressive chemical substance is described by parameters set up in a three-dimensional coordinate system:

$\delta_D$ for dispersion cohesion energy
$\delta_P$ for dipolar cohesion energy
$\delta_H$ for hydrogen bonding cohesion energy The HSP distance, Ra, between polymer and the aggressive chemical substance is given by:

$$Ra^2 = 4(\Delta\delta_D)^2 + \Delta\delta_P^2 + \Delta\delta_H^2$$

The $\Delta$ indicates the difference in the given parameter for the aggressive substance and the polymer.

The relation between the HSP distance, Ra and RED is given as:

$$RED = Ra/Ro$$

Where Ro is the interaction radius, which determines the radius of the sphere in Hansen space, and the center are the three Hansen parameters. All values are calculated or determined with empiric data and it is known to the person skilled in the art how to calculate the values.

The obtained RED value indicates whether or not the polymer is likely to dissolve in the aggressive chemical substance or not:

RED<1 the polymer and the aggressive chemical substance will dissolve

RED=1 the polymer and the aggressive chemical substance will partially dissolve

RED>1 the polymer and the aggressive chemical substance will not dissolve

The resulting RED value is used to give an indication of the likelihood of dissolution or not.

All values can be calculated using the Hansen Solubility Parameter in Practice by (HSPiP) Software, commercially available at http://hansen-solubility.com.

According to the present disclosure the tie layer is selected to provide sufficient adhesion between the base layer and the co-extrusion layer, but also to provide chemical resistance. The tie layer may give melt strength, and, support the co-extrusion coating of both the multi-layered tie layer and the contact layer.

It is preferred that the melting profile of the polymers constituting the tie layer and the polymer(s) constituting the contact layer are in the same range to provide optimal films that do not separate. Preferably all layers comprise polymers that melt at the operating temperature of the process of the present disclosure and even more preferred the melting profiles (i.e. melting points) of the respective polymers should differ by less than 30° C., preferably by 0-15° C., such as 5-15° C.

In one embodiment the tie layer is a multilayer such as made of 2, 3, 4 or 5 layers. In this way, the properties of the film and resulting laminates and packaging's may be improved in terms of the quality of the final laminate film but also to accommodate the specific chemical and physical properties of the contact layer and/or the base layer. Preferably the tie layer consists of two layers.

In one embodiment at least one layer of a multilayered tie layer is selected from ethylene methacrylic acid (EMAA), ethylene acrylic acid (EAA), a terpolymer of ethylene, methacrylic acid and glycidyl methacrylate, terpolymer of ethylene, acrylic ester and maleic anhydride, preferably ethylene, butyl acrylate, and maleic anhydride (t-EBAMA), or, a combination thereof.

In the same or another embodiment another or the second layer of the multilayered tie layer is selected from, a terpolymer of ethylene, acrylic ester and maleic anhydride, preferably ethylene butyl acrylate, maleic anhydride (t-EBAMA), Ethylene methacrylic acid (EMAA), ethylene methyl acrylate (EMA), ethylene butyl acrylate (EBA), ethylene ethyl acrylate (EEA), ethylene acrylic acid (EAA), preferably an ethylene acrylic acid having an acrylic acid content of minimum 10 wt.-% based on the total weight of the ethylene acrylic acid layer (EEA-high acid), or low density poly ethylene (LDPE) or, a combination thereof.

The RED values of the monomers present in t-EBAMA and EAA have for illustration been calculated towards the aggressive chemical substance nicotine, rivastigmine, lidocaine, and fentanyl for illustration. The results are listed in table 1 below.

TABLE 1

RED values for polymers used in the tie
layer according to the present disclosure

| Polymer | monomer | Lido-caine | Riva-stigmine | Nico-tine | Fentanyl |
|---|---|---|---|---|---|
| t-EBAMA | Butyl acrylate | 0.63 | 0.71 | 0.53 | 1.22 |
| t-EBAMA | Maleic anhydride | 1.61 | 1.59 | 1.90 | 4.24 |
| EEA | Methacrylic acid | 1.89 | 1.41 | 1.31 | 3.55 |
|  | Polyethylene | 1.65 | 1.66 | 0.55 | 1.12 |

Each layer of the film or laminate of the present disclosure may be defined by a material such as polymer(s) and its loadings. The skilled person will from the loading and the density of the material used also be able determine the thickness of each layer, if necessary. Most polymers usable in the context of the present disclosure have a density around 1 g/cm$^3$, such as around 0.90 g/cm$^3$ to 1.10 g/cm$^3$.

In table 1 is listed non-exclusive examples of commercially available polymers that may be used as a first or second layer of the multilayered tie layer, or a contact layer with their respective densities.

TABLE 2

Examples of commercial products of polymers
usable according to the present disclosure.

| Name | Abbreviation used | Trademark name | Density[g/cm$^3$] |
|---|---|---|---|
| Cyclic olefin copolymer | COC | Topas ® 8007F-600 | 1.01 (based on ISO 1183) |
| Cyclic olefin copolymer | COC | Topas ® 9506F-500 | 1.01 (based on ISO 1183) |
| Cyclic olefin copolymer | COC | Topas ® 7010F-600 | 1.02 (based on ISO 1183) |
| Polyamide | PA | Selar ® PA 3426R | 1.19 (based on ISO 1183) |
| Ethylene methaacrylic acid | EMAA | Nucrel ® 0609 | 0.93 (based on ASTM D792) |
| Terpolymer of ethylene, butyl acrylate, maleic anhydride | t-EBAMA | Lotader ® 3410 | 0.94 (based on ASTM D1505) |
| Terpolymer of ethylene, butyl acrylate, maleic anhydride | t-EBAMA | Lotader ® 3210 | 0.94 (based on ISO 1183) |
| Ethylene acrylic acid | EAA | Escor ™ 6000 | 0.932 (based on ASTM D1505) |
| Ethylene acrylic acid | EAA-high acid | Escor ™ 5110 | 0.939 (based on ASTM D1505) |

In a further embodiment the layers such as the first layer and the second layer of the multilayered tie layer comprise different polymers.

By having different polymers constituting the first and second tie layers, the laminate film may be optimized to both exhibit improved mechanical properties of the film.

According to the present disclosure it has been found that the loading ratio (g/m$^2$) of the respective tie layers has an effect on the mechanical properties of the film.

Hence, in an embodiment of the present disclosure, wherein the tie layer comprises two layers, the loading ratio (g/m$^2$) of the at least two layers is around 1:1.

In a particular embodiment where the tie layer consists of two layers having a loading of 1:1 the loading of the contact layer is loading$_{contact}$=x*loading$_{tie}$, where x is in the range of 1.33 to 2.75.

The inventors have found that a film with unexpectedly improved mechanical properties is achieved when the loading of the two layers of the multilayered tie layers are approximately equal. At the same time the overall loading could be reduced such as to 4 to 8 or 4-6 g/m$^2$ and thereby saving material and reducing production costs.

In a further embodiment all the layers of the multilayered tie layer are co-extruded with the contact layer for a simplified processing and for ensuring homogeneity of the layers.

The base layer, which is water and/or oxygen resistant, is selected from the group consisting of a metal foil, preferably aluminum foil, a polymer, such as a polymer made from polyamide, polyvinylidene chloride, silicon or aluminium oxide coated polyesters, and/or fluoropolymers.

According to the present disclosure water and/or oxygen resistance is preferably encompassing materials having an oxygen transfer rate (OTR) equal to or below 1 cm$^3$/m$^2$/24 hr/bar according to ASTM standard D3985 at 23° C. and 0% RH and/or water (or moisture) vapor transfer rate (WVTR) equal to or below 1 g/m$^2$24 hr according to ASTM standard F1249 at 38° C. and 90% RH, preferably both the WVTR and the OTR are below 0.01 g/m$^2$/24 hr or 0.01 cm$^3$/m$^2$/24 hr/bar respectively.

According to the present disclosure, the base layer of the film is selected to provide a number of properties to a laminate film and packaging comprising the laminate film. The base layer may give desired barrier and support properties to the final laminate/packaging. Furthermore, the base layer may in one embodiment be a gas and water impermeable base layer, more preferably a water and/or oxygen resistant base layer.

In embodiments where the contact layer is hygroscopic the base layer is preferably made of a metal foil, such as aluminum.

Aluminum is price competitive, a superior barrier to all gases and moisture. Furthermore, similar to other metal-like materials, aluminum has good dead-fold properties, i.e. it does not unfold once folded, it reflects radiant heat, and gives a decorative appeal to laminates and packages.

According to the present disclosure the contact layer must be chemically resistant/inert to the API, such as a so-called aggressive substance and excipient, if present, ultimately to be packaged. Further, the contact layer must show a low absorption of the substances migrating through the film or laminate. The allowed degree of absorption for a given substance is typically dictated by the manufacturer of the substance but often the accepted values lie in the range of 0 to 1% (w/w). For some products up to 10% (w/w) is acceptable typically for products with a low initial API content. The absorption is calculated as the weight of API in a packaging relative to the initial weight of the API in the commercial product.

According to the present disclosure it has been found, contrary to previous beliefs, that the contact layer should have the same or a larger loading than the tie layer. This provides a laminate that shows low absorption but at the same time has improved mechanical properties and is more cost efficient to produce due to the overall lower loading.

Without the wish to be bound by any theory it is believed that contrary to previous theories the contact layer will always take up a certain amount of substance to achieve an equilibrium. By having a contact layer which has a higher general loading and has a loading which is equal to or higher than the loading of the tie layer, it has unexpectedly been found that the API being a highly aggressive compound only absorbs into the contact layer and not the tie layer.

It is believed that when the tie layer has a higher loading and the contact layer a lower loading within specific ranges as has been applied previously with the aim to ensure proper lamination and sealing, the tie layer will act as a sponge that absorbs the compound through the contact layer and therefore the uptake equilibrium with the contact layer is never reached and therefore API continues to be taken up through the contact layer into the tie layer. The present disclosure solves that problem.

The contact layer comprises a polymer selected from the group consisting of a cyclic olefin copolymer (COC), a polyamide (PA), or, an ethylene vinyl alcohol (EVOH).

In a further embodiment a layer of the multilayered tie layer and contact layer comprises a polymer selected from the same group of a cyclic olefin copolymer (COC), a polyamide (PA), or, an ethylene vinyl alcohol (EVOH). The layers may be the same or a different material selected from the above.

The HSP and RED Values calculated using http://hansen-solubility.com, mentioned above resulted in the following values for the preferred polymers according to the present disclosure using lidocaine/rivastigmine as solvent (API):

TABLE 3

HSP and RED values for preferred polymers according to the present disclosure

| Polymer | D | P | H | RED value |
|---|---|---|---|---|
| Lidocaine | 18.1 | 8.2 | 6.1 | — |
| PA 66 | 16 | 11 | 24 | 1.72 |
| COC | 18 | 3 | 2 | 1.32 |
| EVOH | 20.5 | 10.5 | 12.3 | 1.12 |

It has been found that when the contact layer comprises any of the polymers from the group above, having a relatively low RED value (i.e. between 1 and 2) a chemical resistant film and laminate may be obtained even though the mentioned polymers chemically represent different polymer types. Tests have shown that the resistance of laminates in which the film is coated with the preferred polymers show results unexpectedly superior to those of laminates coated/laminated with e.g. the commercial product Barex®.

EVOH is normally used in laminates due to the superior oxygen barrier properties of EVOH. Despite EVOH is known to be very hydrophilic and hydroscopic (i.e. has a high WVTR) it is very suitable according to the present disclosure.

Also, polyamide (PA) has typically been used in laminates due to the superior mechanical properties like tear strength or as a barrier. As for EVOH it is noteworthy that PA may be used as a contact layer and/or co-extrusion layer (i.e. tie and contact layer) for providing a chemical resistant laminate film despite the hydrophilic nature of PA.

In a preferred embodiment where the contact layer is polyamide, the loading of the contact layer is 3 to 27 $g/m^2$, preferably 6 to 10 $g/m^2$, more preferably 8 $g/m^2$. Consequently, the tie layer or plurality of tie layers can be 3-9 $g/m^2$ and in the more preferable embodiment 3-8 $g/m^2$.

Because of the hydrophilic nature of PA and EVOH, in a preferred embodiment, the laminate film obtained according to the present disclosure may be tightly packed in a moisture barrier, in particular if it has to be stored. The laminate film according to the present disclosure may be packed immediately after manufacture and should be kept safely packed until further use, for example in a packing line.

COC has not previously been recognized as being very suitable for extrusion coating and for the production of heat sealable laminates. Without the wish to be bound by any theory this is believed to be due to the stress which the polymer is subjected to during an extrusion process. The stress causes irregular heating and melting within the COC, resulting in the final film or laminate to be unacceptable from a visual point of view in various packaging industries. Hence, it was unexpected when the inventors succeeded in providing a co-extrusion layer comprising COC as a contact layer for sealing aggressive substances.

In another variation the polymer(s) of the tie layer have a melting point that differs from COC by 30° C. or less, preferably by 0-15° C., such as 5-15° C.

In a preferred embodiment, when the contact layer is COC, the loading of the contact layer is 3 to 27 $g/m^2$, preferably 12 to 24 $g/m^2$, more preferably 17 to 24 $g/m^2$. Consequently, the tie layer or plurality of tie layers can be 3-9 $g/m^2$ and in the more preferable embodiment 3-8 $g/m^2$ As an effect of having been able to process a chemical resistant laminate with a co-extrusion layer laminated to a base layer, thin laminates may be obtained, and generally improved processability during the manufacture of the laminates or wrappings is achieved.

Consequently, in an embodiment the multilayered tie layer has a total loading in the range of 3 to 9 $g/m^2$ and/or the contact layer has a loading in the range of 3 to 27 $g/m^2$ and the loading of the laminate is not more than 40 $g/m^2$, more preferably a maximum of 35 $g/m^2$.

In the context of the present disclosure "loading" means the weight of polymer applied/$m^2$. The exact total weight of the final laminate may vary slightly from the loading of the various individual layers.

In a particular embodiment the contact layer of the co-extrusion layer is made from a blend of at least two polymers. Using blends can be a means for reducing the costs and for adapting the physical and chemical properties of the co-extrusion process, such as reducing or increasing the melting temperature to comply with the profile of layers of the tie layer and the polarity of the blend to improve the adhesion properties of the layers and hence the robustness of the final product.

In a preferred embodiment the contact layer consists of one polymer type.

According to an embodiment at least one of or all the polymer(s) forming the contact layer of the co-extrusion layer is a cyclic olefin copolymer, a polyamide, or, an ethylene vinyl alcohol. Each of the polymers are commercially available for example 35 mol % Ethylene-Vinyl Alcohol Copolymer sold under the tradenames EVAL® C109B by Kuraray, an amorphous nylon (polyamide) resin sold under the tradename Selar PA 3426 R by Dupont®, cyclic olefin copolymer, Topas® 6013M-07 sold by Topes®. Other variations of the same functionalities are within the scope of the present disclosure.

In one variation the cyclic olefin copolymer, a polyamide, or, an ethylene vinyl alcohol makes up at least 50% w/w of the blend of the contact layer, preferably at least 60% w/w, more preferably at least 80% w/w, most preferably at least 95% w/w of the contact layer.

According to the present disclosure a film according to the has various applications. In an embodiment of the present disclosure, the film is used to wrap a composition comprising a compound selected from nicotine, fentanyl, lidocaine and rivastigmine, preferably the compound is formulated as a patch, such as a transdermal patch.

According to the present disclosure, when the composition is a patch, the amount of the compound remaining after storage for at least 7 days at 40° C. is a maximum +/−10% (w/w) as compared to the same compound sealed in a similar Barex® patch as index 100.

In a further embodiment the laminate film is heat sealable. A heat sealable laminate film is capable of sealing to itself during heat sealing without creating any deformation of films or laminates. Deformation is undesirable in relation to quality assurance, where any deformation must be noted and explained, which is highly labor intensive. Furthermore, the legislation in many countries is very strict. Hence, films and/or laminates with any deformation are not allowed for packing active ingredients. Therefore, the mechanical properties are very important from a production cost efficiency perspective. Similarly, it is important that the laminates are tight.

A method is also method for providing a laminate film according to the present disclosure, said method comprising the steps of:
i) providing a base layer, which is water and/or oxygen resistant;
ii) co-extruding a layer comprising a tie layer and a contact layer to provide a co-extrusion layer;
iii) coating the co-extrusion layer to the base layer;
iv) allowing the co-extrusion layer coated to the base layer to cure in order to provide the laminate film comprising the multilayered tie layer and the contact layer formed as a co-extrusion layer coated to the base layer;
wherein the contact layer comprises a polymer selected from the group consisting of a cyclic olefin copolymer, a polyamide, or, an ethylene vinyl alcohol, and
wherein the total loading of the tie layer is in the range of 3 to 9 g/m$^2$ and wherein the loading of the contact layer is:

$$loading_{contact} = x^* loading_{tie},$$

where x is in the range of 0.8 to 3, preferably 1 to 3, more preferred 1.33 to 2.75.

In other variations the tie layer is a multilayer, preferably comprising at least two layers, and all the tie layers are coextruded with the contact layer.

In yet an embodiment a first layer of a multilayered tie layer is maximum 5 g/m$^2$.

It has been found that the loading of the first tie layer facing the contact layer is of specific importance to the properties of the final laminate both in terms of adherence, deformation and resistance.

In an embodiment of the method the contact layer has a loading in the range of 3 to 27 g/m$^2$, preferably 8 to 22 g/m$^2$.

In a further embodiment the total loading of the tie layer and contact layer is no more than 40 g/m$^2$, preferably between 6 and 40 g/m$^2$, more preferably no more than 35 g/m$^2$.

In an embodiment the curing of step iv) occurs instantly for example by cooling the co-extrudate in cooling cylinders during the lamination process.

In one embodiment the base layer, which is water and/or oxygen resistant, is selected from the group consisting of metal foil, preferably aluminum foil, polymers, polyamide, polyvinylidene chloride, silicon oxide coated polyesters, and/or fluropolymers.

The contact layer is a polymer selected from the group consisting of a cyclic olefin copolymer, a polyamide, or, an ethylene vinyl alcohol. In yet an embodiment the multilayered tie layer has two layers, and said two layers are the same polymer.

Further, a packaging for packing a composition comprising a compound is provided, said laminate comprises at least:
a first outer layer made of a mechanically wear resistant material;
a laminate film according to the present disclosure, where the base layer side of the laminate film is facing the first outer layer.

In an embodiment the first outer layer may be made from a material selected from but not limited to paper, polyethylene or polyamide based sheets, ortho-phthalaldehyde based sheets, or polyester based sheets, or combinations. It is preferred that the first outer layer is a combination of materials when polyester based sheets are used.

In an embodiment the first outer layer and the laminate film are laminated to provide the packaging. Laminating the first outer layer to the laminate film provides a strong laminate when tested on several parameters, the packaging is easy to wrap, and, it is ensured that the individual parts of the laminates constituting the packaging do not fall apart.

In another embodiment the packaging further comprises a second outer layer facing the exterior side of the first outer layer. Preferably the second outer layer is a paper layer. The paper layer is typically printed with the name, color and/or logo of the product and manufacturer of the product. It is also or alternatively contemplated that the first outer layer can be printed.

It is also contemplated that an adhesive agent may be applied between the second and first outer layers. The adhesive layer may be made of the same or a different material as that of one of the tie layers.

Further suitable adhesives are adhesives approved for use in packaging products for human use and are well known to the skilled person. A suitable adhesive may be selected from but is not limited to polyurethane based adhesives, epoxy based adhesives, or acryl based adhesives.

The laminate of the present disclosure must be inert and impermeable to the compound which the laminate is enclosing. Hence, in an embodiment of the present disclosure a maximum of 10% (w/w), preferably a maximum of 5% (w/w), even more preferably a maximum of 1.5% (w/w), most preferably a maximum 0.5% (w/w) of the compound has migrated into the laminate film after 12 weeks of storage at 40° C.

In a further embodiment the laminate film encloses a compound selected from the group consisting of nicotine, rivastigmine, fentanyl and lidocaine. These compounds are known as aggressive chemicals/compounds and require specialized packaging.

The present disclosure also relates to a method for packaging a composition comprising a compound, said method comprising the steps of:
a) optionally providing an outer layer;
b) providing a laminate film according to the present disclosure;
c) placing a composition comprising a compound on the contact layer side of the laminate film; and
d) sealing the outer layer and/or the laminate film, preferably by heat sealing, in such a way to provide a hollow interior space for sealing the composition, said hollow space having an interior side and an exterior side, wherein the interior side of the film is the contact layer of the co-extrusion layer and the exterior side of the film is the base layer and/or the first and second outer layers.

It is contemplated that a first and/or second outer layer is laminated to the laminate film before steps c) and d) for example in one combined co-extrusion and laminating step.

In a preferred embodiment the compound of the composition is selected from the group consisting of nicotine, lidocaine, rivastigmine and fentanyl. The composition comprising the compound may be a patch, preferably a transdermal patch.

A packaging should preferably comply with International standards such as 16 CFR § 1700.20 (for USA) and ISO 8317 (2003) corresponding to DIN EN ISO 8317 (2004) (for Europe). A "packaging" is in the context of the present disclosure intended to mean a complete film or laminate used to pack a chemical compound.

Specific laminate films according to the present disclosure comprise but are not limited to the following specific examples of base layer/tie-layers/contact-layer (the latter three are coextruded): Al/t-EBAMA/EMAA/COC; Al/EMA/EMAA/COC; Al/EBA/EMAA/COC; Al/EEA/EMAA/COC; Al/LDPE/EMAA/COC; AL/t-EBAMA/EAA/COC; AL/LDPE/EAA/COC; AL/EMA/EAA/COC; Al/EMA/t-EBAMA/COC; Al/EBA/t-EBAMA/COC; Al/EEA/t-EBAMA/COC; Al/EAA/EMAA/PA; Al/t-EBAMA/EMAA/PA; Al/EMAA/EMAA/PA; Al/EAA/t-EBAMA/PA; Al/EMAA/t-EBAMA/PA.

In an embodiment of the present disclosure wherein the tie layer comprises ethylene acrylic acid, the ethylene acrylic acid preferably has an acrylic acid content of more than 8 wt.-%, more preferably above 10 wt.-% based on the weight of the ethylene acrylic acid layer.

Specific films according to the present disclosure that are resistant to nicotine comprise but are not limited to the following specific examples of base layer/tie-layers/contact layer (the latter three are coextruded): Al/t-EBAMA/EMAA/COC; Al/EMA/EMAA/COC; Al/EBA/EMAA/COC; Al/EEA/EMAA/COC; Al/LDPE/EMAA/COC; AL/t-EBAMA/EAA/COC; Al/LDPE/EAA/COC; AL/EMA/EAA/COC; Al/EMA/t-EBAMA/COC; Al/EBA/t-EBAMA/COC; Al/EEA/t-EBAMA/COC; Al/EAA/EMAA/PA; Al/t-EBAMA/EMAA/PA; Al/EMAA/EMAA/PA; Al/EAA/t-EBAMA/PA; Al/EMAA/t-EBAMA/PA.

In an embodiment of the present disclosure, wherein the film is resistant to nicotine and the contact layer is a COC and the base layer is aluminum, the tie-layer is a multilayer of a terpolymer of ethylene, acrylic ester and maleic anhydride and a copolymer of ethylene methacrylic acid.

In an embodiment of the present disclosure, wherein the contact layer is a COC and the base layer is aluminum, the tie-layer is a multilayer of a terpolymer of ethylene, acrylic ester and maleic anhydride and a copolymer of ethylene methacrylic acid, the loading of acrylic ester and maleic anhydride is maximum 8 $g/m^2$, preferably 4 $g/m^2$, the loading of ethylene methacrylic acid is maximum 8 $g/m^2$, preferably maximum 6 $g/m^2$, more preferably maximum 4 $g/m^2$, and wherein the total of the tie layer is maximum 9 $g/m^2$.

In a further embodiment of the present disclosure, wherein the film is resistant to nicotine and the contact layer is a PA and the base layer is aluminium, the tie-layer is a multilayer of a copolymer of ethylene and methacrylic acid, the loading of ethylene and methacrylic acid is maximum 6 $g/m^2$, preferably 3 $g/m^2$, and a copolymer of ethylene acrylic acid, preferably the loading of ethylene acrylic acid is maximum 9 $g/m^2$, preferably 3 $g/m^2$, and wherein the total of the tie layer is maximum 9 $g/m^2$.

In yet another embodiment of the present disclosure, wherein the film is resistant to nicotine and the contact layer is an EVOH and the base layer is aluminium, the tie-layer is a multilayer of EVOH and/or a terpolymer of ethylene, acrylic ester and maleic anhydride.

Specific films according to the present disclosure that are resistant to rivastigmine comprise but are not limited to the following specific examples of base layer/tie-layers/contact layer (the latter three are coextruded): Al/t-EBAMA/EMAA/COC; Al/EMA/EMAA/COC; Al/EBA/EMAA/COC; Al/EEA/EMAA/COC; Al/LDPE/EMAA/COC; Al/t-EBAMA/EAA/COC; Al/LDPE/EAA/COC; Al/EMA/EAA/COC; AVEMA/t-EBAMA/COC; Al/EBA/tEBAMA/COC; Al/EEA/t-EBAMA/COC; Al/EAA/EMAA/PA; Al/t-EBAMA/EMAA/PA; Al/EMAA/EMAA/PA; Al/EAA/t-EBAMA/PA; Al/EMAA/t-EBAMA/PA.

In an embodiment of the present disclosure, wherein the film is resistant to rivastigmine and the contact layer is a COC and the base layer is aluminium, the tie-layer is preferably a multilayer of a terpolymer of ethylene, acrylic ester, and maleic anhydride and a copolymer of ethylene methacrylic acid.

In a further embodiment of the present disclosure, wherein the film is resistant to rivastigmine and the contact layer is a PA and the base layer is aluminium, the tie-layer is preferably a copolymer of ethylene and acrylic acid or a copolymer of ethylene methacrylic acid.

Specific films according to the present disclosure that are resistant to lidocaine comprise but are not limited to the following specific examples of base layer/tie-layers/contact layer(the latter three are coextruded): Al/t-EBAMA/EMAA/COC; Al/EMA/EMAA/COC; Al/EBA/EMAA/COC; Al/EEA/EMAA/COC; Al/LDPE/EMAA/COC; Al/t-EBAMA/EAA/COC; Al/LDPE/EAA/COC; Al/EMA/EAA/COC; Al/EMA/t-EBAMA/COC; Al/EBA/t-EBAMA/COC; Al/EEA/t-EBAMA/COC; Al/EAA/EMAA/PA; Al/t-EBAMA/EMAA/PA; Al/EMAA/EMAA/PA; Al/EAA/t-EBAMA/PA; Al/EMAA/t-EBAMA/PA.

In an embodiment of the present disclosure, wherein the film is resistant to lidocaine and the contact layer is a COC and the base layer is aluminium, the tie-layer is preferably a multilayer of a terpolymer of ethylene, acrylic ester and maleic anhydride and a copolymer of ethylene methacrylic acid.

In a further embodiment of the present disclosure, wherein the film is resistant to lidocaine and the contact layer is PA and the base layer is aluminium, the tie-layer is a multilayer of a copolymer of ethylene and methacrylic acid and a copolymer of ethylene acrylic acid.

Specific films according to the present disclosure that are resistant to fentanyl comprise but are not limited to the following specific examples of base layer/tie-layers/contact layer (the latter three are coextruded): Al/t-EBAMA/EMAA/COC; Al/EMA/EMAA/COC; Al/EBA/EMAA/COC; Al/EEA/EMAA/COC; Al/LDPE/EMAA/COC; Al/t-EBAMA/EAA/COC; Al/LDPE/EAA/COC; Al/EMA/EAA/COC; Al/EMA/t-EBAMA/COC; Al/EBA/t-EBAMA/COC; Al/EEA/t-EBAMA/COC; Al/EAA/EMAA/PA; Al/t-EBAMA/EMAA/PA; Al/EMAA/EMAA/PA; Al/EAA/t-EBAMA/PA; Al/EMAA/t-EBAMA/PA.

In an embodiment of the present disclosure, wherein the film is resistant to fentanyl and the contact layer is a COC and the base layer is aluminium, the tie-layer is preferably a multilayer of a terpolymer of ethylene, acrylic ester and maleic anhydride and a copolymer of ethylene methacrylic acid.

In a further embodiment of the present disclosure, wherein the film is resistant to fentanyl and the contact layer is PA and the base layer is aluminium, the tie-layer is preferably a multilayer of a copolymer of ethylene and methacrylic acid and a copolymer of ethylene acrylic acid.

The present disclosure should not be restricted to the above combinations. Further combinations are within the scope of the present disclosure.

Conveniently, polymers usable in the present disclosure are conventional and thereby easy accessible from various suppliers thereby providing a cost efficient production.

DETAILED DESCRIPTION

The laminate film and packaging according to the present disclosure is intended for use in packaging highly aggressive substances such as nicotine, rivastigmine, fentanyl or lidocaine, however, the present disclosure should not be limited to these specific substances.

The term "film" or "laminate film" according to the present disclosure contemplates a product comprising a base layer coated with a co-extrusion layer comprising one or more tie layers and a contact layer, or, a base layer laminated with one or more tie layers and a contact layer.

A "packaging" is in the context of the present disclosure intended to mean a final laminate used to pack a substance.

The term "highly aggressive compound" should be understood as a compound which is both very reactive with metals, acids, bases or functional groups such as ketones, alcohols, hydro carbons and/or esters, and/or, volatile but also easily migrates through barriers. Similarly, the term "aggressive chemical resistant film" means a film which when in contact with an aggressive substance does not allow more than 1.5% w/w of nominal content to migrate to the packaging material or that 90-110% w/w of the aggressive chemical substance remains in the product when compared to Barex® as index 100.

The term "oxygen and water resistant" as used in the context of the present disclosure contemplates material for which the oxygen transfer rate (OTR) and/or water vapor transfer rate (WVTR) is no more than 1 preferably no more than 0.1 as also indicated above. The term WVTR may also be referred to as the moisture vapor transfer rate (MVTR). WVTR and MVTR are equivalent.

The term "mechanically wear resistant layer" as used to describe the first outer layer should be understood as a material which is suitable for the manufacture of a flexible packaging. The mechanically wear resistant layer may be chosen from but are not limited to materials such as polyethylene or polyamide based sheets, ortho-phthalaldehyde based sheets, or polyester based sheets or combinations.

Further, the mechanically wear resistant material, i.e. the first outer layer, can be provided as a film that is biaxially oriented to give the packaging a higher seal strength. The term "biaxial oriented" should be understood such that the provided polymer film has been stretched in both a longitudinal and a transverse direction during manufacturing.

The term "exterior side" should be understood in its broadest sense. The term exterior environment is used for defining the direction opposite of the side that is facing the composition or compound to be sealed by the laminate or packaging of the present disclosure. This means that the term exterior environment is independent on whether additional layers are coated, laminated or otherwise attached to the film. Thus, the word is used for specifying in which direction a side of a layer is facing.

The various embodiments of the present disclosure will now be illustrated with references to the figures and examples.

Figure 1:
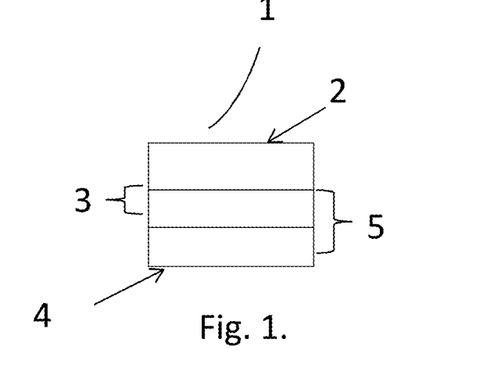
FIG. 1 is a cross section of an embodiment of a chemical resistant film according to the present disclosure.

With reference to FIG. 1 a film of the present disclosure will now be described in greater detail. The film, 1, is obtained by providing a base layer, 2, a co-extrusion layer, 5, said co-extrusion layer comprising a tie layer, 3, and a contact layer, 4, which is coated to one side of the base layer, 2, according to the method of the present disclosure and is allowed to cure/adhere thereto. The base layer, 2, and the co-extrusion layer, 5, define the laminate film according to the present disclosure. Consequently, the laminate film comprises a base layer, 2, and a co-extrusion layer 5, wherein the base layer, 2, is intended for facing the exterior environment, and the co-extrusion layer, 5, is intended for facing the composition/compound to be sealed.

The co-extrusion layer may be coated to the base layer of e.g. aluminium, by a co-extrusion system generally known in the art to provide the co-extrusion layer coated on the first side of the aluminum base layer. The co-extrusion layer may be applied in an amount of maximum 40 $g/m^2$, preferably maximum 30-40 $g/m^2$.

The co-extrusion is preferably performed at a temperature of 240-330° C., more preferred 270-300° C. The speed of the application/coating is in the range of 150 to 600 m/min. The equipment suitable for extruding and laminating films and laminates according to the present disclosure may be obtained from Bobst.

Figure 2:
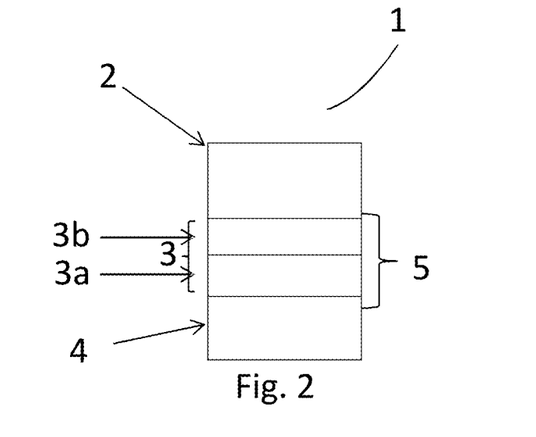
FIG. 2 is a cross section of another embodiment of a chemical resistant film according to the present disclosure.

In another embodiment the tie layer comprises two layers as illustrated in FIG. 2. The laminate film, 1, is obtained by providing a base layer, 2, then laminating thereto a co-extrusion layer, 5, comprising a two-layered tie layer, 3, comprising a first layer, 3a, and a second layer, 3b, and a contact layer 4. The co-extrusion layer is coated onto one side of the base layer, 2, according to the method of the present disclosure and is allowed to solidify/cure.

In the embodiment illustrated, the tie layer, 3, comprises two layers according to the present disclosure. These layers may be made of EMAA as the first tie layer, 3a, having a loading of 4 $g/m^2$ and EAA as the second tie layer, 3b, having a loading of maximum 5 $g/m^2$ so that the total loading of tie layer does not exceed 9 $g/m^2$. The first layer of EMAA faces the contact layer, 4, made of e.g. polyamide having a loading of 9 to 27 $g/m^2$, the second layer made of EAA facing the base layer, 2.

The laminate film according to the present disclosure is intended for use as a component of a packaging suitable for sealing a highly aggressive substance. The film may constitute the packaging itself.

Figure 3:
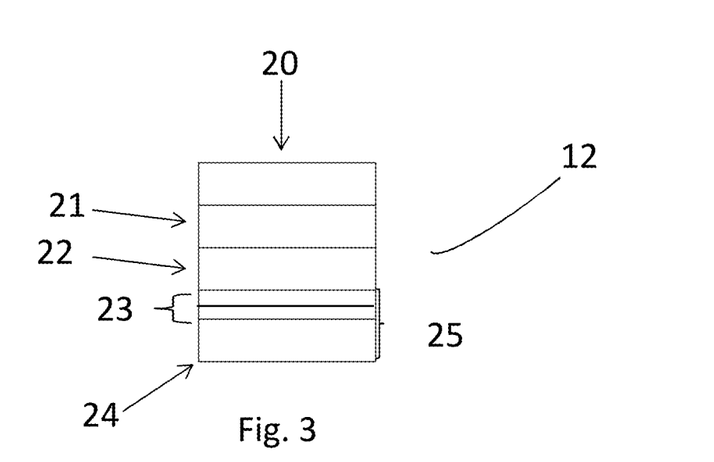
FIG. 3 is a cross section of a laminate according to the present disclosure.

To further improve the mechanical wear resistance of the film a first outer layer may be laminated to the base layer side of the film or simply be wrapped around the film to provide a laminate. Hence, in FIG. 3 is illustrated a cross section of an embodiment of a laminate, 12, according to the present disclosure comprising a first outer layer, 21, a base layer, 22, and a co-extrusion layer, 25. The first outer layer, 21 and the base layer side, 22, may be laminated together before, during or after the co-extrusion layer, 25, is applied/coated to the base layer.

The first outer layer, 21, is a mechanically wear resistant layer which adds safety properties to the wrapping ensuring that the wrapping is not inadvertently opened. Hence, the first outer layer can also be seen as a child proof layer meaning that the first outer layer is made of a material and is sealable in such a way that it is difficult for children to open. Additionally, the outer layer may be provided with a second outer layer, 20.

The second outer layer, 20, is typically a paper layer, wherein the paper layer is facing the exterior environment; the exterior facing side of the second outer layer may be printed as desired. The second outer layer, such as a paper layer, is added to improve the stiffness of the packaging in addition to providing a printing platform.

Furthermore, it is within the inventive concept of the present disclosure that an adhesive agent is applied between the first outer layer and the base layer and/or between the first outer layer and the second outer layer. The obtained packaging may then be assembled in such a way that the various layers do not separate during handling, printing and/or packaging of the substance to be packed.

After production, the film, laminate or packaging may be stored as rolls ready for use in further lamination or packaging of a composition to be packed.

In use, the packaging is sealed around the composition to be packed so that the contact layer of the co-extrusion layer faces the interior side and the composition, and, the base layer, first outer layer or second outer layer, as applicable, face the exterior side, so as to create a hollow interior for containing the, composition.

The sealing of the packaging is achieved in such way that the contact layer of the co-extrusion layer is facing the composition so that the remaining part of the packaging is protected by the contact layer of the co-extrusion layer. In this way, the composition is held within the interior of the packaging and will therefore only have direct contact with the contact layer of the co-extrusion layer.

In general, the order in which the different layers of the packaging according to the present disclosure are applied to the base layer is flexible. Hence, the first outer layer may be applied before the co-extrusion layer is added and the other way around. The order depends on which production line is suitable in a specific situation.

According to all aspects of the present disclosure the base layer may be selected from but not limited to a metal foil, preferably aluminum foil, a polymer, such as a polymer made from polyamide, polyvinylidene chloride, silicon or aluminium oxide coated polyesters, and/or fluro polymers, such as commercial Alu foil from e.g. Hydro, or AlOx coated PET films obtainable from e.g. Toray Films Europe, or SiOx coated PET films obtainable from e.g. Celplast under the tradename Ceramis.

According to all aspects of the present disclosure each of the tie layers of the, optionally multi layered, tie layer may be made of a material selected from ethylene methacrylic acid (EMAA), ethylene acrylic acid (EAA), preferably an ethylene acrylic acid having an acrylic acid content of minimum 10 wt-% based on the total weight of the ethylene acrylic acid layer (EEA-high acid) terpolymer of ethylene, acrylic ester and maleic anhydride, preferably ethylene, butyl acrylate, maleic anhydride (t-EBAMA), a terpolymer of ethylene, acrylic ester and maleic anhydride, preferably ethylene, butyl acrylate, maleic anhydride (t-EBAMA), terpolymer of ethylene, methacrylic acid and glycidyl methacrylate, ethylene methyl acrylate (EMA), ethylene butyl acrylate (EBA), ethylene ethyl acrylate (EEA), or low density poly ethylene (LDPE).

Such polymers described above are available as the commercial products Lotader® 3410 sold by Arkema or Nucrel® 0609HSA sold by Dupont®, or Escor™ 6000 sold by ExxonMobil.

According to all aspects of the present disclosure the contact layer may be made of a material selected from cyclic olefin copolymer, a polyamide, or, an ethylene vinyl alcohol or mixtures thereof, such as the commercial products EVAL® C109B sold by Kuraray, Selar PA 3426 R sold by Dupont® or COC 6013M-07, COC 8007F-600, 7010E-600 or 9506F500 sold by Topas® or EVOH obtainable from Nippon Gohsei under the tradename Soarnel®.

According to all aspects of the present disclosure the first outer layer may be made of a material selected from paper, polyethylene or polyamide based sheets, ortho-phthalaldehyde based sheets, or polyester based sheets, or combinations, such as the commercial product F-PAP sold by Flexpet.

The present disclosure will now be illustrated in more details with reference to the following non limiting examples.

RED Calculation

Determination of the HSP values and interaction radius for nicotine, rivastigmine, fentanyl and lidocaine requires that the solubility of the drug is evaluated against at least 16 solvents having a range of polar and hydrogen bonding properties. The methodology of determining HSP values, interaction radius and RED values are described in C. M. Hansen: "Hansen Solubility Parameters, A User's Handbook", CRC Press, 2007, Second Edition and exemplified in EP 2 895 531.

Typical solvents used to determine the HSP may be but is not limited to the solvents present in table 2.

TABLE 2

Typical solvents used to determine the HSP of a polymer or substance of interest. Typical solvents used in Determining of HSP of rivagstigmine, lidocaine, fentanyl and nicotine

| Chemical name | Trade Designation or Alternate Name |
|---|---|
| Acetonitrile | Acetonitrile |
| Ethylene glycol n-Butyl Ether | Butyl CELLOSOLVE ™ Glycol Ether |
| Dibutyl Ether | Dibutyl Ether |
| Dimethyl Formamide | Dimethyl Formamide |
| Dimethyl Sulfoxide | Dimethyl Sulfoxide |
| Methanol | Methyl alcohol |
| 2-Butanone | Methyl Ethyl Ketone |
| 4-Methyl-2-pentanone | Methyl Isobutyl Ketone |
| n-Butyl Acetate | n-Butyl Acetate |
| n-Heptane | n-Heptane |
| 1-Propanol | n-Propyl Alcohol |
| o-Dichlorobenzene | 1,2-Dichlorobenzene |
| Tetrahydrofuran | Tetrahydrofuran |
| Toluene | Methylbenzene |
| Propylene Carbonate | Propylene Carbonate |
| Water | Water |

For assessing the solubility of rivastigmine, lidocaine, fentanyl and nicotine in the solvents an experimental measurement can be performed. The solubility is assessed based on the visual observation of 0.5 g of the chemical substance in a vial with 5 $cm^3$ solvent at room temperature. The vial is capped with a polyethylene-lined lid and labeled with the solvent loaded. The vials are placed in a vial shaker at low speed at room temperature. After 24 hours, the samples are removed from the vial shaker, and allowed to sit for 30 min before they are visually rated. The rating is performed by giving each solvent a score being 0 for insoluble and 1 for soluble. The numerical ratings are then entered into the HSPiP software program to obtain the HSP (Hansen solubility parameters). R (radius) values for the compound of relevance, e.g. nicotine, rivastigmine, fentanyl and/or lidocaine is inserted, and a report is generated.

The report lists the final parameters and R values calculated for nicotine, rivastigmine, fentanyl and/or lidocaine. The report also lists the solvents used in the evaluation, their HSP values (taken from a database), the rating of the visual observations, and their RED values with a specific polymer of interest. In a similar manner RED values can be calculated for other compounds.

EXAMPLES

Examples 1 and 2 are embodiments of a film according to the present disclosure. The film comprises a base layer connected to a tie layer comprising two layers (a first tie layer and a second tie layer), wherein the first layer of said tie layer is connected to the contact layer. The film according to the present disclosure has an ordered structure of:

Base layer/tie layer 2/tie layer 1/contact layer the latter three layers are coextruded in accordance with the method of the present disclosure to form a co-extrusion layer.

In both examples the co-extrusion layer is co-extrusion coated to the base layer so that the contact layer has a surface intended to be in contact with a composition comprising a compound selected from nicotine, rivastigmine, fentanyl, or lidocaine and wherein such composition may be in the form of a transdermal patch.

Example 1

Example 1 is a film having COC (commercial product Topas® 8007F600) as a contact layer with a loading of 22 g/m$^2$. The first layer of the multilayered tie layer is a copolymer of ethylene methacrylic acid (Nucrel® 0609HSA) having a loading of 4 g/m$^2$. The second layer of the multilayered tie layer is a terpolymer of ethylene, butyl acrylate, and maleic anhydride (Lotader® 3410) having a loading of 4 g/m$^2$. The base layer is aluminium foil. The total loading of the multilayered tie layer and the contact layer being 30 g/m$^2$.

The film had good mechanical properties cf. the below and was easy to produce.

Example 2

Example 2 is a film having PA (Seler® PA 3426R) as the contact layer with a loading of 8 g/m$^2$. The first layer of the tie layer is a copolymer of ethylene methacrylic acid (Nucrel® 0609HSA) having a loading of 4 g/m$^2$. The second layer of the tie layer is a copolymer of ethylene acrylic acid (Escor™ 5110) having a loading of 4 g/m$^2$. The base layer is aluminium foil. The total loading of the multilayered tie layer and the contact layer being 16 g/m$^2$.

The film had good mechanical properties cf. the below and was easy to produce.

Example 3

Sample 3 is a film having COC (copolymer-Ehtylene1-norbornene, Commercial product, Topas® 8007F-600) as the contact layer with different loadings as shown below, 22, 22 and 12 respectively.

In a first film, a first layer of the tie layer was a copolymer of ethylene methacrylic acid (Nucrel® 0609HSA) having a loading of 4 g/m$^2$. The second layer of the tie layer was a copolymer of ethylene acrylic acid (Lotader® 3410) having a loading of 4 g/m$^2$. The base layer was aluminium foil. In a second and third laminate film only one layer of tie layer was included.

Testing with nicotine as API, the following was found re the laminates' performance.

TABLE 3

| Laminate # | Tie 2 | Tie 1 | Contact | Result, API uptake |
|---|---|---|---|---|
| 1 | 4 | 4 | 22 | Ok |
| 2 |   | 8 | 22 | Ok |
| 3 |   | 18 | 12 | Not ok* |

*Uptake was higher than the specified upper limits.

Alternative commercial COC products include but are not limited to: Topas® 9506F-500, Topas® 7010E-600 (works in terms of API uptake but requires higher welding temperatures than the other two).

Example 4

Similar to the above, different laminate films were made all including outer layers and base layer to mimic a commercial product. The laminate films were produced with varying applications of co-extrudates according to the present disclosure (inv.) and comparative extrudates not part of the present disclosure (comp.), as shown in Table 4.

All laminate films were thus made of PETW36/PE14/AL9 as the outer layers and base layer. The co-extruded layers were composed of;

Tie layer 2: Nucrel® 0609HSA (an ethylene methacrylic acid)
Tie layer 1: Escor® 5110 (an ehtylene acrylic acid)
Contact layer: Selar® PA 3426R (a polyamide)

TABLE 4

| Film #/ application g/m$^2$ | Tie layer 2 | Tie layer 1 | Total tie | Contact layer | Total application | |
|---|---|---|---|---|---|---|
| 1 | 1 | 1 | 2 | 8 | 10 | Comp. |
| 2 | 3 | 3 | 6 | 8 | 14 | Inv. |
| 3 | 4 | 4 | 8 | 8 | 16 | Inv. |
| 4 | 7 | 7 | 14 | 12 | 26 | Comp. |
| 5 | 4 | 4 | 8 | 18 | 22 | Inv. |
| 6 | 4 | 4 | 8 | 22 | 30 | Inv. |
| 7 | 4 | 4 | 8 | 24 | 32 | Inv. |
| 8 | 8 | 8 | 16 | 40 | 56 | Comp. |

Thus, films no. 1, 4 and 8 were not according to the present disclosure either because 1) the contact layer was too thick (four times the tie layer), 4) the total tie layer was too thick and the ratio tie/contact outside range, i.e. contact layer too thin; and 8) the total tie layer too thick and also the total loading too high, ratio tie/contact however within range.

Methods

The mechanical properties of the laminate films of table 4 were tested. The following properties were tested:
Tear strength
Puncture resistance on both sides
Sealing strength
Lamination strength
Exploration test All tests were made according to industry standards and with some modifications as detailed below:

Tear strength—according to ASTM D1937-14 with no modifications.

Puncture resistance—according to ASTM F1306 with the following modifications: sample diameter 48 mm instead of 34.9 and puncture tool tip diameter 3.0 mm instead of 3.2 mm). The resistance should be at least 50N.

Sealing strength according to DIN 55529 with no modifications.

The sealing strength test was made of three tests:
Trial 1: 150° C., 5 bar pressure, 0.5 seconds
Trial 2: 180° C., 5 bar pressure, 0.5 seconds
Trial 3: 150° C., 5 bar pressure, 0.1 second Lamination strength according to ASTM D903-98(2010) with the following modifications: Sample width was 15 mm instead of 25 mm, samples were not conditioned to 23° C. +/−1° C., 50% RH+/−2%. Instead all samples were kept at the same place and thus continuously kept under identical conditions. The pull speed was set to 100 mm/min instead of 305 mm/min. The measuring angle was 90° not 180°.

The exploration strength test was made as follows: a four side sealed bag was sealed with parameters 150° C., 0.3 seconds and 3 bar pressure, with a size of 80 mm×90 mm including a 5 mm wide sealing area.

Figure 4:
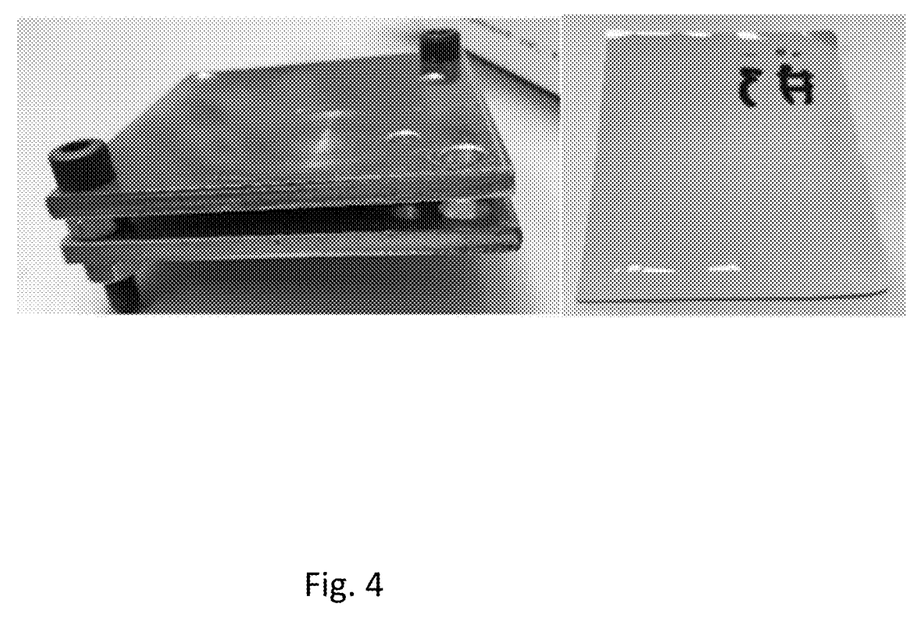
FIG. 4 is a picture illustrating the set-up of the exploration test referred to in example 4.

The bag was held between two pieces of iron with a gap of 5 mm (se picture in FIG. 4), and were penetrated with a syringe connected to a pressure device. The bag was then inflated to a pressure of 0.4 bar.

The success criteria for a given laminate is to withhold the pressure for 40 seconds without bursting.

The results of all the tests made is given in table 5.

Sample 1 showed a lamination strength of 1.5N/15 mm. Since there was only loaded 1 g/m² of each tie layer the lowest lamination strength which is too low to be acceptable, app. 2 being the lowest acceptable for the purpose. Sample 2 also had a low loading of tie-layers which is generally lower than those described in the prior art but surprisingly these samples showed laminations strengths on the same level as samples three to seven above the acceptable threshold of app. 2. Sample 8 with the highest total loading could be expected to have the highest laminations strength which surprisingly turned out not to be the case. Without the wish to be bound by any theory it is believed that to be able to apply such high loadings allows the melt to be cooled slightly in the airgap, thereby decreasing lamination strength.

Regarding sealing strength, the results show an increase in sealing strength following an increase in the contact layer part of the co-extrudate until a certain level. Once the layer becomes too thick more energy is needed to seal, and as a result sample 8 does not seal properly under all usual conditions. Sample No. 8 thus has a narrow operation window constraining the machine specifications in the production.

This observation could also be confirmed by the exploration test in which sample No. 8 as the only sample failed. Sample 7 however with a high loading performed well and just as good as sample 1-6 on the sealing test.

In conclusion, from the combined results of the mechanical tests it could be seen that samples 1 and 8 did not fulfill all requirements since the respective lamination strengths were too low. Hence, it appears that there is limits as claimed

TABLE 5

| No. | Coating loading (g/m²) | Tear Strength (Machine direction) (N) | Tear Strength (Cross direction) (N) | Puncture resistance Front side (N) | Puncture resistance Sealing side (N) | Lamination strength (N/15 mm) | Sealing strength #1 (N/15 mm) | Sealing strength #2 (N/15 mm) | Sealing strength #3 (N/15 mm) | Exploration test |
|---|---|---|---|---|---|---|---|---|---|---|
| 1 | 10 | 0.7 | 0.4 | 65.8 | 58.9 | 1.5 | 8.0 | 7.6 | 7.6 | ok |
| 2 | 14 | 0.9 | 0.5 | 70.4 | 62.0 | 5.1 | 8.7 | 9.2 | 9.3 | ok |
| 3 | 16 | 0.7 | 0.5 | 68.8 | 65.7 | >5 | 10.8 | 10.3 | 9.9 | ok |
| 4 | 26 | 0.8 | 0.6 | 71.1 | 72.3 | 4.5 | 16.4 | 15.4 | 12.0 | ok |
| 5 | 22 | 0.7 | 0.4 | 71.6 | 70.4 | 2.2 | 15.7 | 13.9 | 14 | ok |
| 6 | 30 | 1.2 | 0.5 | 67.6 | 67.9 | 3.7 | 16.6 | 16.9 | 11.9 | ok |
| 7 | 32 | 0.8 | 0.5 | 76.1 | 73.2 | 2.4 | 19.9 | 17.5 | 9.5 | ok |
| 8 | 56 | 1.1 | 0.9 | 84.2 | 88.3 | 1.7 | 26.5 | 23.7 | No Seal | Fail |

Discussion

Tear strength levels from 0.7 to 1.2 indicate that the main influencer for this parameter is the substrate on which the coating is applied, i.e. the base layer and outer layers, since there is no significant increase following coating weight increase.

When looking on puncture resistance samples 1 to 7 showed puncture resistance from 65.8N to 76.1N (front side) and 58.9N to 73.2N (sealing side), while sample 8 with the very thick coating showed an increase to 84.2 and 88.3 respectively. It was surprising to note that even with a loading as thin as 10 g/m² (sample 1) mechanical properties on the same level as larger loadings was obtained. However, increasing the total loading of the tie layer to 16 g/m² and the total loading to 56 increased the puncture resistance, even though the impact on tear resistance was much less. Hence, on this test it was the upper limits which had an effect of the properties.

as regards the relation between tie layers and contact layers. It is also evident from the tests that there is an upper limit to the total layers.

Experiments have shown that the laminate in use in such cases will take up too much API, cf. example 3. Thus, even if sample 4 has satisfactory mechanical properties the update will be too high and the laminate sample cannot be used as intended.

What is claimed is:

1. A packaging for packing a composition, comprising:
a first outer layer made of a mechanically wear-resistant material;
an aggressive chemical-resistant laminate film comprising a base layer and a coextrusion layer, wherein:
the base layer is one or more of water-resistant or oxygen-resistant;
the coextrusion layer comprises a tie layer and a contact layer, wherein the contact layer comprises a polymer selected from the group consisting of: a polyamide, an ethylene vinyl alcohol, or any combination thereof, and wherein a total loading of the tie layer is between 3 g/m$^2$ and 9 g/m$^2$ and a loading of the contact layer is equal to x times the total loading of the tie layer, wherein x is in a range of 1 to 3, and the base layer side of the film faces the first outer layer;

wherein the aggressive chemical-resistant laminate film is resistant to a chemical selected from nicotine, fentanyl, rivastigmine, or lidocaine.

2. The packaging of claim 1, wherein the aggressive chemical-resistant laminate film encloses the composition.

3. The packaging of claim 1, wherein the base layer is selected from aluminum, polyvinylidene chloride, a silicon oxide-coated polyester, an aluminum oxide-coated polyester, an aluminum oxide polyethylene terephthalate-coated (PET) film, a silicon oxide-coated PET film, or any combination thereof.

4. The packaging of claim 1, wherein the composition is a patch.

5. The packaging of claim 1, wherein the composition is in a liquid state.

6. A method for providing an aggressive chemical-resistant laminate film, comprising:
providing a base layer, wherein the base layer is one or more of water-resistant or oxygen-resistant;
coextruding a tie layer and a contact layer to provide a coextrusion layer;
coating the coextrusion layer to the base layer; and
curing the coextrusion layer coated to the base layer, wherein:
the contact layer comprises a polymer selected from the group consisting of: a polyamide, an ethylene vinyl alcohol, or any combination thereof, and
a total loading of the tie layer is between 3 g/m$^2$ and 9 g/m$^2$ and a loading of the contact layer is equal to x times the total loading of the tie layer, wherein x is in a range of 1 to 3;
wherein the aggressive chemical-resistant laminate film is resistant to a chemical selected from nicotine, fentanyl, rivastigmine, or lidocaine.

7. The method of claim 6, wherein:
the tie layer comprises a plurality of layers,
each layer of the plurality of layers of the tie layer are coextruded with the contact layer.

8. The method of claim 6, wherein the tie layer and the contact layer are coextruded at a temperature between 240° C. and 330° C.

9. The method of claim 6, wherein the base layer is selected from aluminum, polyvinylidene chloride, a silicon oxide coated polyester, an aluminum oxide coated polyester, an aluminum oxide polyethylene terephthalate (PET) film, a silicon oxide coated PET film, or any combination thereof.

10. A method for providing a packaging for packing a compound or a composition, comprising:
providing a first outer layer made of a mechanically wear-resistant material;
providing an aggressive chemical-resistant laminate film comprising a base layer and a coextrusion layer, wherein providing the aggressive chemical-resistant laminate film comprises:
providing the base layer, wherein the base layer is one or more of water-resistant or oxygen-resistant,
coextruding a tie layer and a contact layer to provide the coextrusion layer,
coating the coextrusion layer to the base layer, and
curing the coextrusion layer coated to the base layer, wherein:
the contact layer comprises a polymer selected from the group consisting of: a polyamide, an ethylene vinyl alcohol, or any combination thereof, and
a total loading of the tie layer is between 3 g/m$^2$ and 9 g/m$^2$ and the loading of the contact layer is equal to x times the total loading of the tie layer, wherein x is in a range of 1 to 3,
wherein the aggressive chemical-resistant laminate film is resistant to a chemical selected from nicotine, fentanyl, rivastigmine, or lidocaine; and
attaching the aggressive chemical-resistant laminate film to the first outer layer, wherein the base layer side of the aggressive chemical-resistant laminate film faces the first outer layer.

11. The method of claim 10, further comprising:
providing the compound or the composition;
sealing the packaging around the compound or the composition to be packed so that the contact layer side of the coextrusion layer faces the interior side and the compound or the composition.

12. The method of claim 10, wherein the base layer is selected from aluminum, polyvinylidene chloride, a silicon oxide coated polyester, an aluminum oxide coated polyester, an aluminum oxide polyethylene terephthalate (PET) film, a silicon oxide coated PET film, or any combination thereof.

13. The method of claim 10, wherein the compound or the composition is a patch.

14. The method of claim 10, wherein the compound or the composition is in a liquid state.

* * * * *